United States Patent [19]

Nordin

[11] Patent Number: 4,774,831
[45] Date of Patent: Oct. 4, 1988

[54] METHOD AND A DEVICE FOR DETERMINING MOISTURE CONTENT

[76] Inventor: Ulf Nordin, Mazurkavägen 4, S-663 02 Hammarö, Sweden

[21] Appl. No.: 919,246
[22] PCT Filed: Jan. 21, 1986
[86] PCT No.: PCT/SE86/00017
§ 371 Date: Nov. 4, 1986
§ 102(e) Date: Nov. 4, 1986
[87] PCT Pub. No.: WO86/04412
PCT Pub. Date: Jul. 31, 1986

[30] Foreign Application Priority Data

Jan. 25, 1985 [SE] Sweden ............... 8500346

[51] Int. Cl.⁴ ................................. G01N 25/00
[52] U.S. Cl. ............................ 73/75; 73/73; 374/45
[58] Field of Search .............. 73/73, 75; 374/45

[56] References Cited

U.S. PATENT DOCUMENTS

| | | | |
|---|---|---|---|
| 1,508,516 | 4/1927 | Harvey | 73/75 |
| 1,623,675 | 9/1924 | Harvey | 73/75 |
| 2,362,344 | 11/1944 | Baver et al. | 73/75 |
| 2,611,974 | 9/1952 | Stratveit et al. | 73/73 |
| 2,718,141 | 9/1955 | Richards | 73/75 |
| 2,874,482 | 2/1959 | Haltmeier | 73/75 |
| 3,517,549 | 6/1970 | Teich | 73/73 |
| 3,813,927 | 6/1974 | Furgason | 73/73 |
| 4,408,482 | 10/1983 | Zhuravlev et al. | 73/75 |
| 4,532,797 | 8/1985 | Yang | 73/75 |

FOREIGN PATENT DOCUMENTS

| | | | |
|---|---|---|---|
| 0371493 | 11/1973 | U.S.S.R. | 73/75 |
| 0867828 | 5/1961 | United Kingdom | 73/75 |
| 1329602 | 9/1973 | United Kingdom | 73/73 |

*Primary Examiner*—William A. Cuchlinski, Jr.
*Assistant Examiner*—Thomas B. Will
*Attorney, Agent, or Firm*—Murray and Whisenhunt

[57] ABSTRACT

The present invention relates to a method and a device for determining the moisture content in a moist material in the form of particles or pieces, such as sand, gravel, dry mortar, coal, chips, and the like. In accordance with the invention, partly the cooling effect of the material on a measuring body (1, 35, 41, 50), performing in the material, at a temperature above the boiling point of the liquid, is recorded, the material and the measuring body moving in relation to each other, and partly the cooling effect of the material on a measuring body (2), performing in the material, at a temperature below the boiling point of the liquid, is recorded. The comparison between the two recordings results in a relation, which gives a measure as to the moisture content.

11 Claims, 6 Drawing Sheets

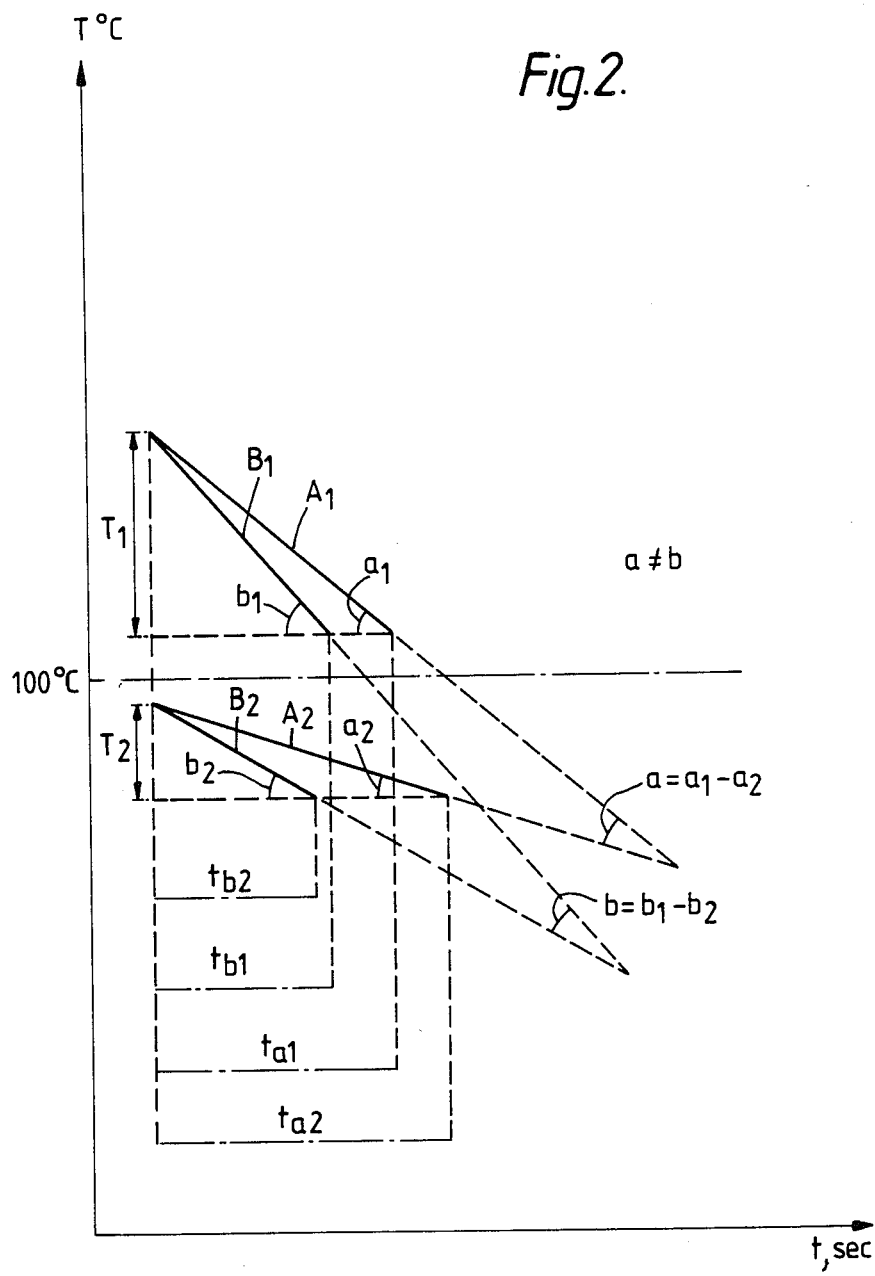

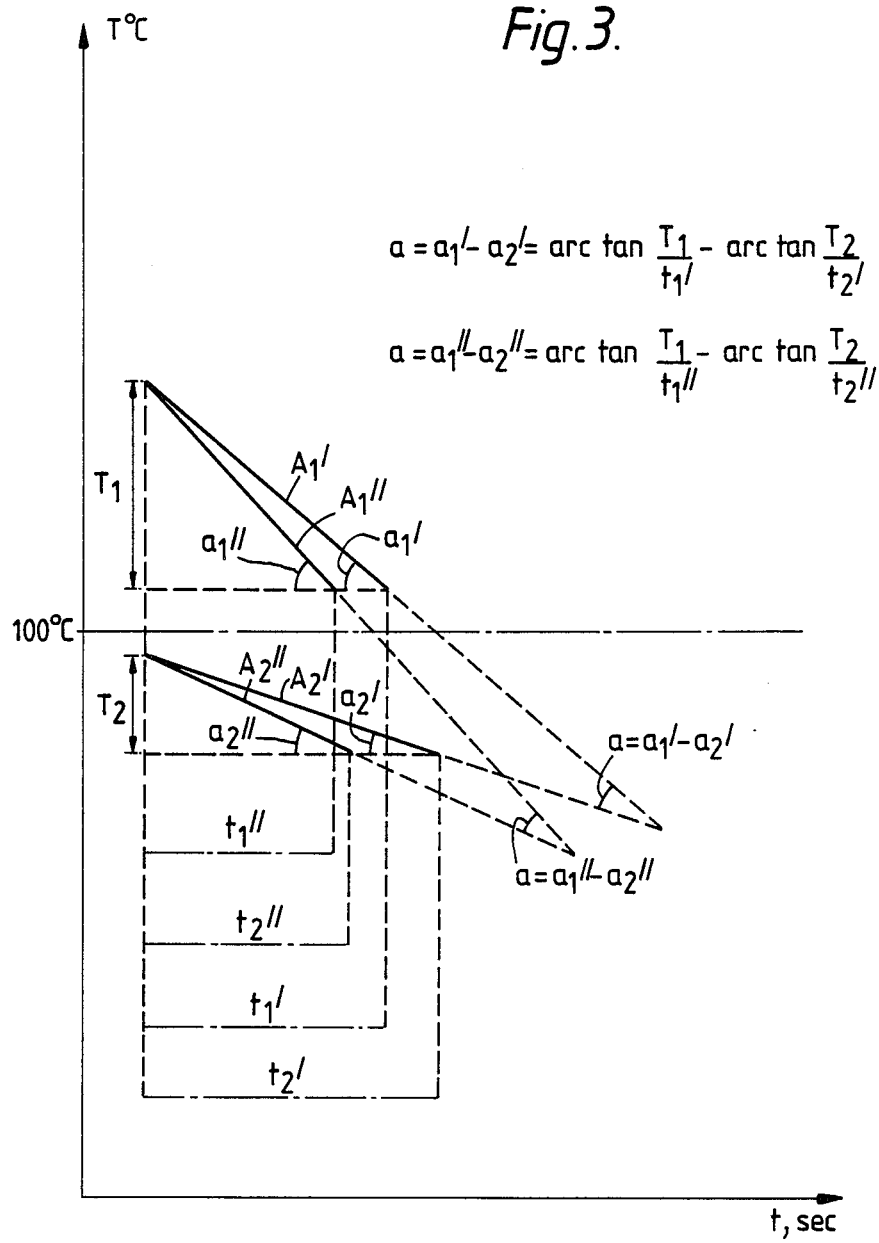

METHOD AND A DEVICE FOR DETERMINING MOISTURE CONTENT

THE TECHNICAL FIELD

The present invention relates to a method and a device for determining the moisture content in a moist material in the form of particles or pieces more clearly expressed a material, the particles of which have a moist surface, i.e. consists of a mixture consisting of the particles and a liquid on the surface of the particles and/or between the particles, and which, during the measurement, are moving in relation to the measuring device. Such materials are e.g. flowing sand and gravel, particularly sand and gravel, which may be included as aggregates in concrete or dry mortar, i.e. mixtures of binders, e.g. lime and/or cement an.d aggregates. Other possible materials are solid fuels of various types. The invention can also be applied to determine the surface moisture content of crop materials of various types, such as chopped whole grains, cereals etc.

THE BACKGROUND OF THE INVENTION

In many situations there is a need for determining, quickly and reliably, the moisture content of a material in the form of particles. Such a material can be a component in a mixture having particular mixing proportions, which is to be dried to attain a certain maximum moisture content, etc. A few examples will be stated below in order to illustrate the range of application of the invention.

When road surfacings are produced, the main ingredient being asphalt, stones and gravel are used as aggragates, which are added to the asphalt according to various formulae. Before the aggregate material is added to the asphalt material, it is dried and heated to a selected temperature, which is quite important for the quality and the hardness of the end product. The furnace is heated with oil burners, which are adjusted depending on the temperature variations, which are measured along the furnace. This control technique means that the temperature of materials, which have already left the furnace, is gauged. However, it is desirable to be able instead to gauge the moisture content in and the temperature of the fed material in order to adjust the burner in view of this and be able to reduce the oil consumption.

When dry mortar is produced, the conditions are similar to the conditions, when road surfacing is produced, but there is a difference, that the temperature after the drying of the aggregate material must be as low as possible. The object is to consume energy to dry the aggregate material but not more than that. At temperatures above what is needed energy is lost to the environment. Also, an elevated posttemperature causes problems for the transport equipment after the drying process.

When concrete is produced, it is important that the amount of water in the aggregate material is determined quickly and carefully, since this water greatly influences the amount of water to be added afterwards. The water in the aggregate material may vary from a few per cent, when using a dried aggregate material, to as high as 30-40% of the total amount of water in the completed concrete mixture. The ratio between cement and water in the completed concrete must be kept within selected limits in order to attain the desired quality. In case there is uncertainty as to the amount of water, often too much cement is added. Consequently, a careful determination of the amount of water is of great economic importance when producing concrete. Also, a wrong amount of water impairs the concrete and sometimes it may render it useless, resulting in rejections.

In the stone-working industry it has been found that the moisture content influences the milling process, when stone powder of various types is produced. Consequently, the artisan wants to be able to vary the mutual adjustment of the grinding bodies as the moisture content varies, partly to obtain a uniform quality and partly to reduce the consumption of wear metals.

In the cellulose industry quick lime is used in some processes and it is recycled by burning it in lime sludge furnaces. The lime is charged into the furnaces in the form of dehydrated sludge, the moisture content of which varies due to the condition of the filters, the particle size of the lime etc. Large amounts of energy are needed for the burning in the lime sludge furnaces and in order to be able to adjust the burners and consequently to lower the amount of fuel it is advantageous to thoroughly be aware of the moisture content of the charged material.

When chips, peat, coal etc. are burned the moisture content of the fuel is an important factor of the combustion in the boiler. An apporpriate air supply in relation to the heat value and the moisture content results in a superior economy and an exceedingly small amount of air-contaminants. Customarily the boiler is adjusted by i.e. gauging the flue gas temperature. It is quite obvious that it may already have been damaged, when high temperatures are recorded, and it would be advantageous to be able to gauge the moisture content of the fuel, in order to control the boiler in advance.

In order to solve the above stated and similar problems it is a must to be able to quickly and carefully determine the moisture content of the material. When producing concrete today prevailingly a sample method is used to determine the moisture content of the aggregate material. This means that sampling is performed with certain intervals, the moist material is weighed, dried and weighed again, in order to obtain a measure of the moisture content. Obviously, this method is slow and tedious and also not reliable, since the aggregate flow through the plant is so large, that when the sampling outcome has been obtained, the aggregate, which is to be fed to the mixer, may be an entirely different aggregate from the one when the sampling was performed. It is also obvious that this sampling method can not be used in those instances, when speed is an important factor, e.g. when adjusting boiler plants etc.

Hence, also considerably quicker gauging methods have been developed. In one method of this kind radroactive isotopes are used in order to count the number of water molecules within a sphere of a container, in which the moist material is kept. A drawback of this method is that it partly gauges a material, which due to the flow conditions in a silo is not used but remains there, and partly also gauges the water of crystallization and that amount of water, which is bound in the granules due to capillary effects and consequently does not influence the concrete production.

Another suggested method is based on the idea of gauging fluctuations in electric conductivity for different moisture contents. However, this method is unreliable due to the fact, that the inherent electric characteristics of the material strongly influences the measurement result.

It is also known how to use the heating capacity of the material in order to determine the moisture content. Such a method and appropriate equipment are described in DE-OS No. 31 47 195. In accordance with the method, which is described in this patent specification, a measuring body, which is inserted in a stationary material, e.g. leather or another fibrous material, is heated, first to a certain selected preheating temperature of between 40° and 90° C. Subsequently the measuring body is heated to a certain selected temperature of between 90° and 140° C. in order to dry the enveloping material. The drying time, which is dependent on the moisture content, is recorded. By comparing the recorded drying time and earlier recorded calibration times, a measure of the moisture content is obtained. However, also this method is characterized by some definite restrictions. The most serious restriction is that the method can not be used for flowing materials.

DESCRIPTION OF THE INVENTION

The object of the present invention is to develop a quick and reliable method as well as an equipment suitable for the method to determine the moisture content of moist materials in the form of particles or pieces. A particular purpose is to be able to continuously or intermittently gauge the moisture content of flowing materials. The most important feature of the invention is that partly the cooling effect of the material on a measuring body performing in the material is recorded at a temperature above the boiling point of the liquid, the material and the measuring body moving in relation to each other, and partly the cooling effect on a measurirg body performing in the material at a temperature below the boiling point of the liquid is recorded, and that by comparing the two recordings a correlation is obtained, which gives a measure of the moisture content. This can be achieved by mathematically processing the measurement figures with the guidance of some relations between cooling effects and moisture content, which are found by calibration measurements. It is fair to say that the measurement figures, which are used in these calculations, are relative measurements of the rate and/or the size of the enthalpy change of the moist material above and below the boiling point respectively of the liquid, which has moistened the material.

According to the invention preferably two measuring bodies are used, partly the cooling effect of the material on one of the measuring bodies, which is kept at a temperature above the boiling point of the liquid, being recorded and partly the cooling effect of the material on the other measuring body, which is kept at a temperature below the boiling point of the liquid, being recorded and then the difference between these cooling effects being recorded. The time needed for the cooling of the bodies between two selected temperatures, above and below the boiling point respectively, can e.g. be measured, which gives a measure of the cooling rate, or expressed differently, the rate of the enthalpy change of the passing material, below and above the boiling point respectively. One alternative is to supply energy to the bodies and keep the temperature constant. In this case the supplied energy is measured and is a measure of the cooling effect. A third alternative is to supply a constant amount of energy to the measuring bodies and record the temperature changes or, expressed in another way, the size of the enthalpy changes of the material, the moisture content of which is to be measured. A fourth alternative is to measure the time needed to heat the cooling bodies frm a low to a high temperature within the temperature ranges, above and below the boiling point respectively. However, in this case also the supplied amount of energy must be measured in order to obtain a measure of the cooling effects above and below the cooling point respectively. Also combinations and alternatives are possible.

The cooling of the measuring bodies is influenced by several factors, e.g. the heating of the material due to heat radiation and convection from the heating element, heating of ambient air, heating and evaporation of moisture on the surface of the body etc. The invention is founded on the basic principle that the influence of the moisture content on the cooling effect is separated from the rest of the cooling effects and that the cooling effect of the moisture content is transformed to measurable values, which accordingly state the moisture content. To be able to accomplish this separation the specific characteristics of the moistening liquid are used. For the sake of simplicity it is assumed in the following discussion that said liquid is water, but the method may be employed for most liquids.

The temperature of water, which at atmospheric pressure is heated, the supplied energy being constant, increases mainly in a continuous fashion up to 100° C. and then supplied energy is used to evaporate the water and the temperature of the water is kept constant at 100° C. In case a measuring body is heated to e.g. 200° C. and its temperature is allowed to drop e.g. to 125° C., an important part of the cooling effect is used to evaporate the water on or close to the measuring body. The amount of evaporated water is dependent on i.e. the moisture content of the material. In order to determine this the time period for the temperature drop is recorded in accordance with the first embodiment described above. However, the cooling period is influenced also by other factors than the moisture content. In order to have the evaporation effect separated from other cooling effects, an identical measuring body is disposed in parallel with the first, but the second measuring body has a starting temperature of lower than 100° C. Also in this case and in accordance with the embodiment the time period for a selected temperature drop is recorded, from a temperature of below 100° C. to an even lower temperature. The measurement result from the measurement in the lower temperature range gives a characterization as to the medium, in which the measuring device is performing, i.e. it takes into account such factors as the ambient temperature, the temperature of the investigated material, its granularity, the movement of the material etc. However, the heat of evaporation does not influence the second measuring body. Consequently, what is achieved with the two measuring bodies is a recording of relative measurements of the enthalpy change rate of a moist material at temperatures above and below respectively the boiling point of the liquid, which has moistened the material. By comparing these values a relation is obtained, which is used to calculate the actual moisture content with the guidance of some functional relations, found by calibration measurements, between cooling effects and moisture contents. These known functional relations have been obtained by calibration measurements based on known moisture contents, which have been obtained by carefully conducted measurements, e.g. by measurements before and after the drying of the material. Said calibrations with the guidance of known functional relations can be conducted manually by means of tables and graphs but preferably is conducted in a computer, which can give directly readable values of the moisture content or directly guide a process, e.g. for controlling liquid feed or for adjusting a burner in a drying plant.

The above-mentioned principles can also be used in the above-mentioned alternative methods and combinations thereof.

Additional features and aspects as well as advantages of the invention are stated in the patent claims as well as in the following description of some embodiments.

BRIEF DESCRIPTION OF THE DRAWINGS

In the following description reference will be made to the accompanying drawings, in which:

FIG. 2 illustrates relations between temperature and cooling time, when a measuring body is cooled in a granulate, which is moistened with water, with different moisture contents and temperature ranges;

FIG. 3 shows cooling conditions in materials having the same moisture content, the ambient conditions however being different;

DESCRIPTION OF PREFERRED EMBODIMENTS

Figure 1:
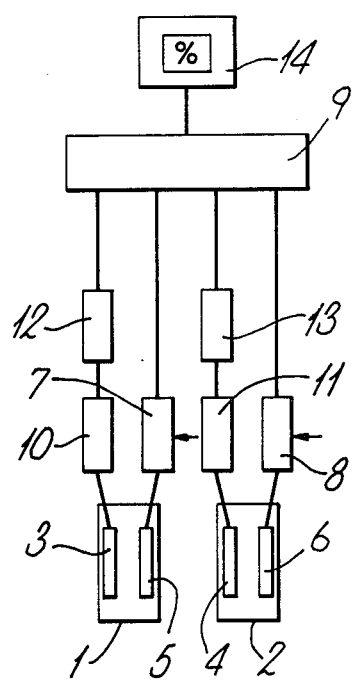
FIG. 1 is a block diagram, which schematically illustrates the principle of the measuring method according to a first preferred embodiment, which is based on a recording of the cooling speeds, in a moistened granulate, of a heated body, which is immersed in the granulate and to which no amount of energy is supplied during the measuring process.
Figure 8:
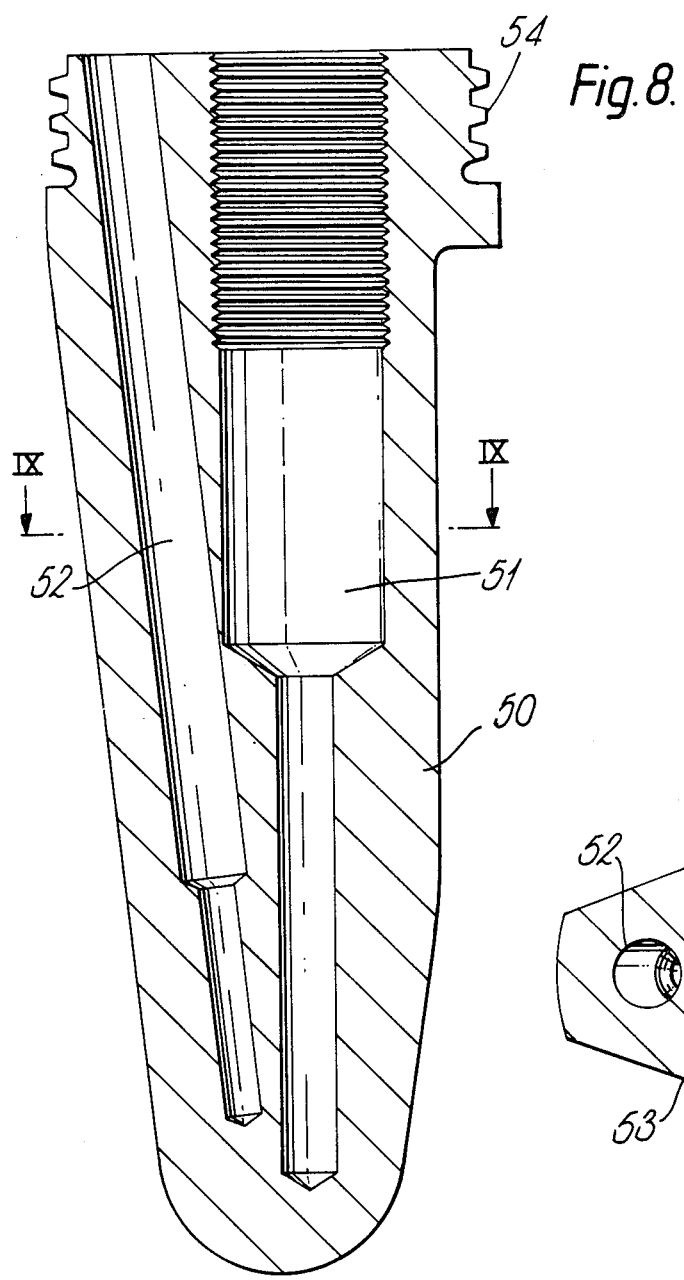
FIG. 8 shows in more detail how the gauging tip can be designed according to an embodiment.
Figure 9:
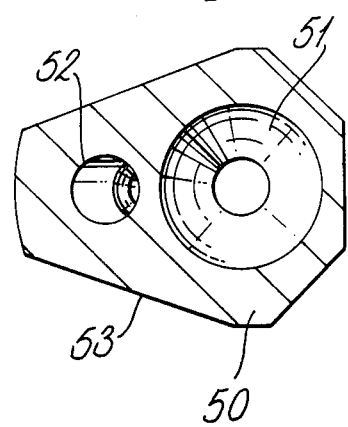
FIG. 9 is a cross section IX—IX in FIG. 8.

FIG. 1 shows a first measuring body 1 and a second measuring body 2. The two measuring bodies 1 and 2 are identical and may be designed as is shown in FIGS. 8 and 9. Each measuring body 1 and 2 includes temperature measuring sensors 3 and 4 respectively and heating pins 5 and 6 respectively. The heating pins 5 and 6 can heat measuring bodies 1 and 2 to a selected temperature above and below the boiling point of the liquid respectively, with which the flowing material has been moistened, in which the measuring bodies are immersed during the measurement. As an example, a D.C. voltage of twelve volts can be applied to the heating pins 5 and 6 via power amplifiers 7 and 8 respectively, which are controlled by a computer 9. The measuring values from the measuring sensors 3 and 4 are amplified in signal amplifiers 10 and 11 respectively and are transformed in analog-to-digital-converters 12 and 13 respectively to digital signals, which are transmitted to computer 9. A display unit 14 as well as an alarm unit to communicate with an operator is also connected to computer 9.

The method of operation of the equipment schematically shown in FIG. 1 is as follows. The material, the moisture content of which is to be determined, may be a mixture of stones and sand, which contains a certain amount of water, and the moisture content will be measured while the material is flowing along a conveying belt. The two measuring bodies 1 and 2, which preferably are made of stainless steel, are heated to a temperature of above 100° C. and below 100° C. respectively by means of heating pins 5 and 6 respectively. When the selected temperature has been reached, e.g. 200° C. on the first measuring body 1 and 50° C. on the second measuring body 2, which is recorded by means of measuring sensors 3 and 4, measuring bodies 1 and 2 are simultaneously immersed in the flowing material. The temperature of heating bodies 1 and 2 immediately starts to drop but at different rates. The cooling rates of the bodies 1 and 2 are influenced by the rate of flow of the material, grain size, ambient temperature as well as the inherent thermal conductivity of the measuring bodies etc. An additional factor, which influences the cooling, is the moisture, which the material contains. However, the moisture content influences the cooling of the first measuring body 1 quicker than the second measuring body 2, despite the fact that the measuring bodies are identical. The reason for this difference is that the first measuring body 1, which is kept at a temperature above 100° C. during the entirety of the measuring process, also evaporates water contacting the surface of measuring body 1. As is well known the heat of evaporation of water is considerable, which evidently influences the cooling rate. However, the second measuring body 2 is cooled all the time at a temperature below the boiling temperature of water, which does not involve any evaporation of water close to measuring body 2. Time $t_{a1}$ required to lower the temperature of the first measuring body 1 from e.g. 200° C. to 125° C. is recorded by the computer. The cooling rate of measuring body 1 during the first measurement is represented by line $A_1$ in FIG. 2. The slope of line $A_1$, angle $a_1$, is arc tan $(T_1/T_{a1})$. In the same manner slope $a_2$ of line $A_2$, arc tan $(T_2/t_{a1})$, is recorded in computer 9, which line represents the cooling rate of second measuring body 2, when the cooling takes place from e.g. 50° C. to 30° C. Slope $a_2$ of line $A_2$ is smaller than slope $a_1$ of line $A_1$. The difference between the slopes of lines $A_1$ and $A_2$, angle $a_1$, represents the evaporation of the water and is a measurement of the moisture content. Or more distinctly expressed, the actual moisture content is, in principle, a linear function of the measured value of the angular difference. Some constants, which are included in the expression for this functional relation, have been calculated by measuring known moisture contents and have been fed into the memory unit of the computer. These constants are calibration values for the measuring equipment, which have been fed into the computer. By processing the measuring values in the computer in accordance with a program introduced into the computer it is then possible to automatically obtain the actual moisture contents. The moisture content is set forth on display unit 14, in which the moisture can be expressed e.g. as a percentage having one or several decimals, preferably one decimal, which is a sufficiently exact determination of the moisture content for most technical applications.

FIG. 2 shows also a second measurement at another, higher moisture content. In this case lines $B_1$ and $B_2$, which represent the cooling of the first and the second measuring body respectively, are steeper and also the difference angle b is larger than angle a in the preceding case, which in the computer gives the actual measure of the moisture content according to the same in principle linear functional relation as in the preceding case.

In case a few other conditions other than the moisture content are changed, e.g. the ambient temperature, the cooling process of the first measuring body 1 as well as of the second measuring body 2 is influenced. But the influence of the moisture content on the cooling process is not influenced. This is illustrated in FIG. 3, where the curves $A_1'$ and $A_2'$ illustrate the cooling of measuring bodies 1 and 2 at a certain higher ambient temperature and the curves $A_1''$ and $A_2''$ represent the cooling at a somewhat lower ambient temperature. The slope of the lines is somewhat different. However, the difference in slope is the same, since the moisture content is the same. This relation is represented by the difference angle a, which is constant, although other conditions than the moisture content may be changed.

Figure 4:
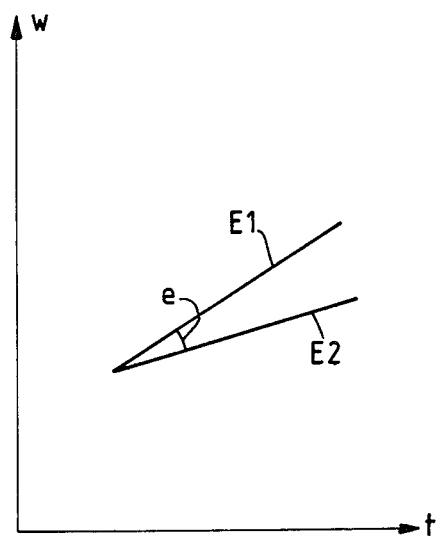
FIG. 4 illustrates in the form of a diagram a second embodiment of the invention, which is based on keeping the temperature constant and measuring the energy consumption due to the cooling effect of the moist granulate on the measuring bodies.

The same equipment as in FIG. 1 can in principle be used in the alternative measuring method, in which the temperature of the two measuring bodies 1 and 2 is kept constant. The temperature of the first measuring body 1 can e.g. be kept constant at 150° C. and the temperature of the second measuring body 2 be kept constant at 50° C. by supplying an electric current to heating pins 5 and 6 respectively. The temperatures are sensed by temperature measuring sensors 3 and 4 and the current supply is controlled in order to keep these temperatures constant. At the same time the supplied energy is measured, FIG. 4, which is represented by curves $E_1$ and $E_2$. The steeper curve $E_1$ represents the energy supply to measuring body 1, which performs at the higher temperature, while the lower curve $E_2$ represents energy supply to measuring body 2, which performs at the lower temperature. The difference in slope, e, is a measurement of the difference in cooling and consequently, also a measurement of the moisture content. In this case too, there is a functional relation, which has been calculated on the basis of known moisture contents and has been introduced into the memory unit of the computer. Thus, the measured value is calculated in computer 9 by means of the calibrated relation, in order to show the wanted moisture content in the material in display unit 14. In principle, the same equipment as in FIG. 1 can also be used, in case the temperature changes during a certain period are measured instead, in which case the energy supply to the measuring bodies is kept constant as is the case with other embodiments of and/or combinations of the described pinciples.

Figure 5A:
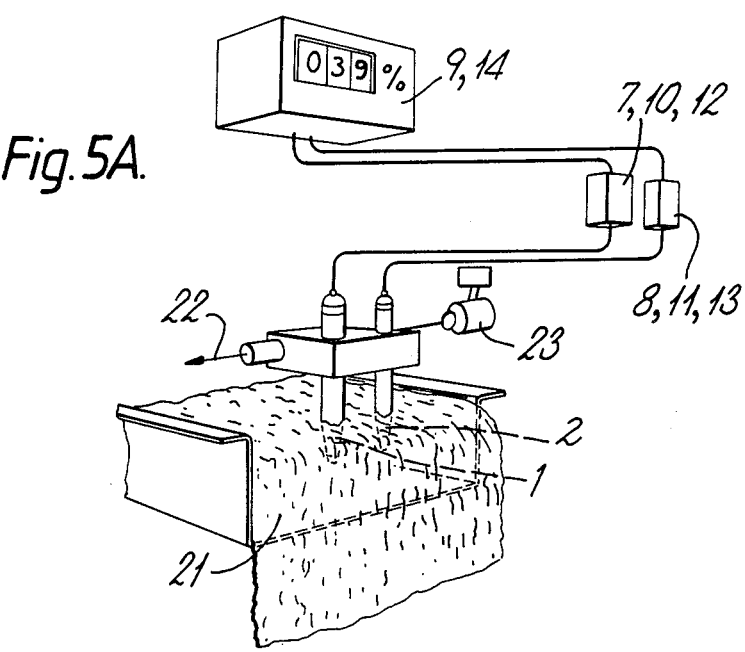
FIGS. 5A and 5B show semi-schematically an equipment according to the invention for measuring the moisture content in a flowing material.
Figure 5B:
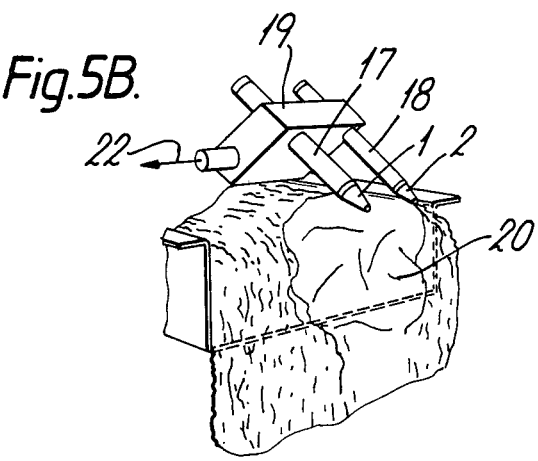

In FIGS. 5A and 5B, the equipment according to the invention is described semi-schematically. The two measuring bodies 1 and 2 are mounted on bars 17 and 18 respectively. The latter are in their turn mounted at a mutual distance of between 50 and 150, preferably about 80 mm, and are disposed in parallel in a holder 19. Holder 19 is suspended by means of a spring in order to let bars 17,18 and their measuring tips 1 and 2 spring away, in case frost lumps or large items 20 in the flowing material 21 pass, and subsequently spring back to their measuring position. The power amplifiers for the heating pin current, the signal amplifiers and the analog-to-digital-converters are represented by the "boxes", which have been denoted by 7,10,12 and 8,11,13 respectively, while the computer and the display unit are represented by a unit denoted by 9,14. Measuring bodies 1,2 are introduced into material flow 21 by turning holder 19 around an axis of rotation 22 by means of an adjustment motor 23, which is controlled by a time relay in computer 9. The frequency of the measurements is determined by adjusting a time relay. Before measuring bodies 1 and 2 are turned into material flow 21 they have been heated to a selected starting temperature above and below 100° C. respectively. When the heated measuring bodies 1 and 2 accordingly are turned into the material flow, the material is allowed to first pass for a few seconds in order to cleanse the measuring bodies. Subsequently the measurement starts in accordance with the first described embodiment by measuring the time necessary to let the temperature drop to a certain lower level for each of measuring bodies 1 and 2 respectively, and then the difference value is calculated automatically and processed in the computer as has been described above in order to obtain a measure of the moisture content. As an alternative measure, the temperature can of course be measured for a certain given period of time, which gives the same cooling value. A larger measuring time gives a more reliable means value of the moisture content, since a greater amount of material is passing measuring bodies 1 and 2. In case the measuring time e.g. is 15 seconds and the feeding rate of the material 21 is 1 m/sec, then an average of the moisture content of the material is measured, which corresponds to a material string on the belt of 15 m in length. The heating time is 15 seconds and subsequently a new measurement can be performed. Consequently, if the flow time in a drying plant, which is fed with material flow 21, is about 3 minutes, then six adjustments of e.g. a burner can be accomplished, the average moisture content value of 50% of the fed material having been measured. In case other measuring times are selected, other values are obtained, e.g. a measurement for 30 seconds, a material string of 30 m, a heating for 15 seconds, 4 adjustments of the burner and a measurement of the average moisture on 66% of the fed material. The selection of measuring times, temperature drops, temperature elevations, energy supply or equivalents, depending on the selection of an embodiment of the measuring method according to the invention, is determined by the size of the plant, variations in moisture content and material qualities, the speed of employed equipments, to make use of the measured values for controlling various functions etc. Consequently, the mathematical functions of the measuring equipment preferably includes also constants, which can be adjusted according to various recipes as to material mixtures, material qualities etc. by means of a key set on a software cabinet, which preferably also houses computer 9. By means of this key set also measuring times, temperature limits etc can be changed.

Figure 6:
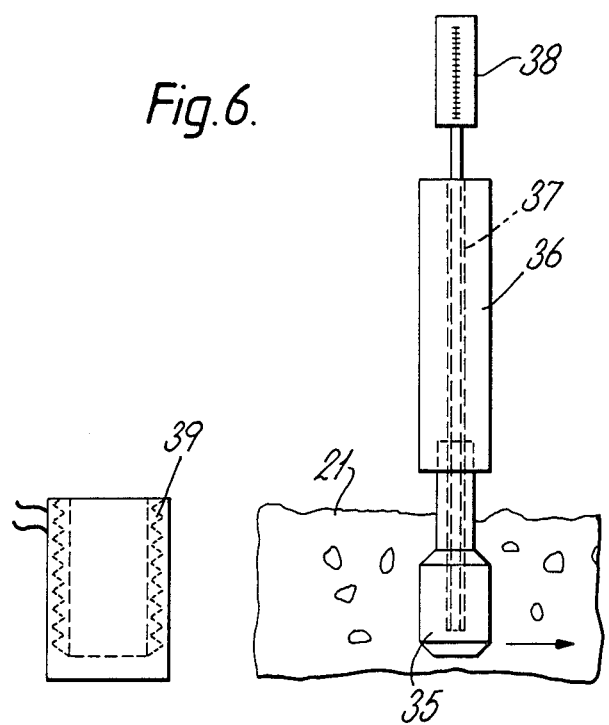
FIG. 6 shows a measuring device having a gauging tip for measuring a temperature drop without a supply of energy during the measurement according to the measuring principles illustrated in FIGS. 1-3.

FIG. 6 shows how measuring bodies 1,2, which so far have been just schematically shown, can be designed. Measuring body 35 in FIG. 6 is made of a metal, preferably stainless steel, or another heat conducting material and is fastened to a handle 36 made of wood, a plastic material or another heat insulating material. A hole 37 extends through the handle and down into measuring body 35 for a thermometer 38 or for a temperature measuring sensor (parts 3 and 4 in FIG. 1). Measuring body 35 can be heated in a heating chamber 39 to its adequate temperature and subsequently it is immersed in material 21, the moisture content of which is to be determined. As an alternative to being heated in a separate heating chamber measuring body 35 can instead be heated by means of a heating pin, which has been mounted inside the heating body, as indicated in FIG. 1.

Figure 7:
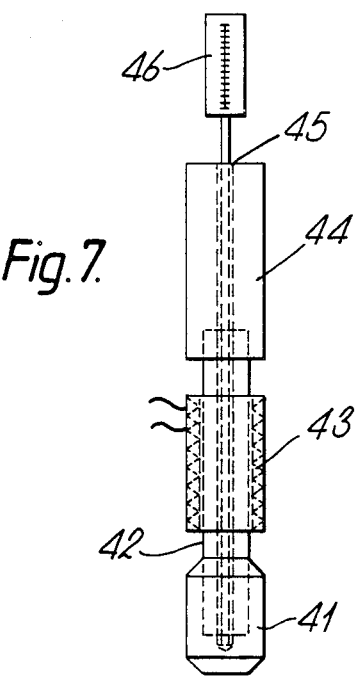
FIG. 7 shows a measuring device having a gauging tip, to which heat energy is supplied in a constant amount, or a gauging, tip, which is kept at constant temperature according to the method illustrated in FIG. 4.

FIG. 7 shows a measuring body 41, which is designed to be used for those forms of the method, in which a constant amount of energy is supplied or the measuring body is kept at a constant temperature. Measuring body 41 is made of a metal also in this case, such as stainless steel, or another heat conducting material and is fastened to a "heat feeder" 42 by means of screwing, soldering, shrinking, or similar fastening methods, which feeder comprises a bar made of copper, aluminum or another material having a satisfactory thermal conductivity. A heat chamber 43 containing electrical resistance wires is disposed on the outside of heat feeder 42. Heat feeder 42 is fastened to a handle 44 of wood, a plastic material or another heat insulating material. A hole 45 for a thermometer 46 or a temperature measuring sensor is drilled through the handle and the heat feeder and down into measuring body 41.

FIGS. 8 and 9 show in more detail how the measuring tip, i.e. measuring body 1,2, can be designed according to an alternative, most preferred embodiment. Measuring body 50 has a major hole 51 for heating pin 5,6 (not shown) and a minor hole 52 for measuring sensor 3,4 (also not shown). The latter hole has an inclination inwardly and consequently, measuring body 50 can have a tapered end and the heat feeding distance from surface 53 of the measuring body to the measuring sensor in hole 52 is short. At its top measuring body 50 is provided with threads 54 and it can be secured to an insulating handle 19 (not shown).

I claim:

1. A method for determining the moisture content of a moist material moist with a liquid, said moist material being in the form of particles and pieces, such as sand, gravel, dry mortar, coal, chips and the like, said method comprising:
   recording the cooling effect of said material on a first measuring body disposed in said material, said measuring body being at a temperature above the boiling point of said liquid, said material and said measuring body moving in relation to each other;
   recording the cooling effect of said material on a second measuring body disposed in said material, said second measuring body being at a temperature below the boiling point of said liquid; and
   comparing the two recordings to obtain a relation resulting in a measure of the moisture content of said moist material.

2. A method according to claim 1, wherein said recordings are processed mathematically with functional relations, obtained by calibration measurements, between cooling effects and moisture content.

3. A method according to claim 1 or 2, wherein there are recorded relative values of the rate and/or the size of the enthalpy change of the moist material above and below respectively the boiling point of said liquid.

4. A method according to claim 1, wherein two similar measuring bodies are used, one of the measuring bodies having a temperature above the boiling point of the liquid and the other measuring body having a temperature below the boiling point of said liquid.

5. A method according to claim 4, wherein there is measured the time needed to cool one of said bodies between two temperatures above said boiling point and the time needed to cool the other of said bodies between two temperatures below said boiling point to provide a measure of the cooling rate above and below respectively said boiling point.

6. A method according to claim 4, wherein during said time measurement, the temperature of the measuring bodies is kept constant above and below respectively the boiling point, by supplying a controlled amount of energy to the measuring bodies, the supplied amounts of energy being measured, the difference as to energy supplied to the two measuring bodies giving a measure of the cooling effect due to the moisture content.

7. A method according to claim 4, wherein the measuring bodies are each supplied with a constant amount of energy and the changes in the temperature of the measuring bodies are recorded.

8. A device for determining the moisture content of a moist material moist with a liquid, said material being in the form of particles or pieces, said device comprising:
   two measuring bodies made of heat conducting materials;
   means for heating the measuring bodies to temperatures above and below respectively the boiling point of said liquid;
   means for measuring the temperature of the measuring bodies;
   means for recording the difference in the cooling effect of said material on said two measuring bodies; and
   means for comparing said difference in the cooling effects to provide a measure of the moisture content.

9. A device according to claim 8, wherein said means for comparing compares said difference with calibrated functional relations between cooling effects and moisture contents of the material.

10. A device according to claim 8 or 9, wherein said measuring bodies are mounted on a common holder and wherein said measuring bodies, when measurements are performed in a flowing material, can be moved aside by large lumps or the like in the material.

11. A device according to claim 9, and further including a computer for calculating the moisture content partly with the recorded difference in the cooling effect of the material on the two measuring bodies and partly with calibrated and functional relations, supplied to the computer, between cooling effects and the moisture content of the material.

* * * * *